US010376621B2

(12) United States Patent
Casas

(10) Patent No.: US 10,376,621 B2
(45) Date of Patent: Aug. 13, 2019

(54) SYSTEMS AND METHODS FOR MAINTAINING FLUID BALANCE

(71) Applicant: HeartWare, Inc., Miami Lakes, FL (US)

(72) Inventor: Fernando Casas, Miami Lakes, FL (US)

(73) Assignee: HeartWare, Inc., Miami Lakes, FL (US)

( * ) Notice: Subject to any disclaimer, the term of this patent is extended or adjusted under 35 U.S.C. 154(b) by 26 days.

(21) Appl. No.: 15/630,373

(22) Filed: Jun. 22, 2017

(65) Prior Publication Data

US 2018/0001005 A1 Jan. 4, 2018

Related U.S. Application Data

(60) Provisional application No. 62/357,460, filed on Jul. 1, 2016.

(51) Int. Cl.
*A61M 1/00* (2006.01)
*A61M 1/10* (2006.01)
*A61M 1/12* (2006.01)

(52) U.S. Cl.
CPC .......... *A61M 1/1086* (2013.01); *A61M 1/122* (2014.02); *A61M 1/1036* (2014.02);
(Continued)

(58) Field of Classification Search
CPC ................ A61M 1/1086; A61M 1/122; A61M 2230/30; A61M 1/1036; A61M 2230/005; A61M 2230/04
See application file for complete search history.

(56) References Cited

U.S. PATENT DOCUMENTS 4,888,011 A * 12/1989 Kung ................. A61M 1/1086
623/3.24
6,234,772 B1 5/2001 Wampler et al.
(Continued)

FOREIGN PATENT DOCUMENTS

WO 20060133409 A2 12/2006
WO 20100099403 A1 9/2010
(Continued)

OTHER PUBLICATIONS

International Search Report and Written Opinion dated Sep. 15, 2017, for corresponding International Application No. PCT/US2017/038760; International Filing Date: Jun. 22, 2017 consisting of 11-pages.

*Primary Examiner* — Scott M. Getzow
(74) *Attorney, Agent, or Firm* — Christopher & Weisberg, P.A.

(57) ABSTRACT

A signal processing circuit for controlling operation of an implanted ventricular assist device comprising an input module for receiving one or more signals of a patient from one or more sensors. A processor for processing the received signals is included, the processor configured to compare a total blood output on a left side of the patient's heart with a total blood output on a right side of the patient's heart; determine at least one from the group consisting of the presence of fluid imbalance between the left and right sides of the patient's heart and the absence of fluid imbalance between the left and right sides of the patient's heart based on the comparison; and when the presence of fluid imbalance is determined, control the implanted ventricular device to restore fluid balance between the left and right sides of the patient's heart.

10 Claims, 3 Drawing Sheets

(52) U.S. Cl.
CPC ... *A61M 2230/005* (2013.01); *A61M 2230/04* (2013.01); *A61M 2230/30* (2013.01)

(56) References Cited

U.S. PATENT DOCUMENTS

| | | |
|---|---|---|
| 6,264,635 B1 | 7/2001 | Wampler et al. |
| 7,699,586 B2 | 4/2010 | LaRose et al. |
| 8,864,644 B2 | 10/2014 | Yomtov |
| 2005/0159639 A1 | 7/2005 | Skliar |
| 2009/0112312 A1 | 4/2009 | LaRose et al. |
| 2012/0245681 A1 | 9/2012 | Casas et al. |
| 2014/0100413 A1 | 4/2014 | Casas et al. |
| 2014/0357937 A1 | 12/2014 | Reyes et al. |

FOREIGN PATENT DOCUMENTS

| | | |
|---|---|---|
| WO | 20120040544 A1 | 3/2012 |
| WO | 2016137743 A1 | 9/2016 |

\* cited by examiner

SYSTEMS AND METHODS FOR MAINTAINING FLUID BALANCE

CROSS-REFERENCE TO RELATED APPLICATION

This application is related to and claims priority to U.S. Provisional Patent Application Ser. No. 62/357,460, filed Jul. 1, 2016, entitled SYSTEMS AND METHODS FOR MAINTAINING FLUID BALANCE, the entirety of which is incorporated herein by reference.

STATEMENT REGARDING FEDERALLY SPONSORED RESEARCH OR DEVELOPMENT n/a

TECHNICAL FIELD

The present invention relates to systems and method for maintaining blood flow balance between the left and right sides of a patient's heart using one or more ventricular assist devices (VADs).

BACKGROUND

A VAD is a device which is used to assist the heart of a mammalian subject such as a human patient. A typical VAD includes a pump which is implanted in the body of the subject. The pump typically has an inlet connected to a source of blood to be circulated, and an outlet connected to an artery. Most typically, the inlet of the pump is connected to the interior of the left ventricle and the outlet of the pump is connected to the aorta, so that the pump operates in parallel with the left ventricle to impel blood into the aorta. The pump may be a miniature rotary impeller pump having an impeller disposed in a pump housing and driven in rotation by a small electric motor which may be closely integrated with the pump. The motor in turn typically is powered by an implantable power source such as a storage battery with an arrangement for charging the battery from an external power source. The VAD typically includes a control system which controls operation of the power source so as to drive the impeller at a set rotational speed and thus provide constant pumping action.

VADs can be used to assist the heart of subjects suffering from conditions which impair the pumping ability of the heart. Such assistance can be provided permanently, or while the subject awaits a suitable heart transplant. In other cases, the assistance provided by the VAD allows the heart to heal. A VAD may be provided to assist with pumping on either or both sides of the patient's heart. For instance, for conditions impairing the ability of the left side of the heart to pump blood into the systemic circulation, the patient may be provided with a left ventricular assist device (LVAD). For conditions impairing the ability of the right side of the heart to pump blood into the pulmonary circulation, the patient may be provided with a right ventricular assist device (RVAD). For conditions impairing both sides of the heart, the patient may be provided with a biventricular assist device (BiVAD).

In many of the above instances, the patient's condition may result in the left and right sides of the heart having disparate outputs. Because the blood output from one side of the heart is received by the other side of the heart, a disparate output between the two sides can result in an unwanted accumulation of blood at the entry to the side of the heart having the lower output. For instance, if the left side of the heart outputs less blood than the right side, blood may accumulate in the patient's lungs, and may even result in pulmonary edema (drowning).

Therefore, it is desirable to provide a method and/or system for monitoring and regulating blood output on both sides of the heart to prevent unwanted accumulations of blood in the cardiovascular system of the patient.

SUMMARY

One aspect of the invention provides for a method for controlling fluid balance between pulmonary and systemic circulations of a patient having one or more ventricular assist devices. The method may involve: determining left ventricular cardiac output, and right ventricular cardiac output; determining an output of blood from a left ventricular assist device of the patient, such that if the patient does not have a left ventricular assist device, the determined output is 0; determining an output of blood from a right ventricular assist device of the patient, such that if the patient does not have a right ventricular assist device, the determined output is 0; measuring a difference between (i) a sum of the left ventricular cardiac output and the output of blood from the left ventricular assist device and (ii) a sum of the right ventricular cardiac output and the output of blood from the right ventricular assist device; and if the value of the measured difference exceeds a predetermined threshold, adjusting a parameter for control of at least one ventricular assist device of the patient.

In some examples, the left ventricular cardiac output may be based at least in part on left atrial pressure, and/or the right ventricular cardiac output is based at least in part on right atrial pressure. In some examples, the output of blood from a ventricular assist device of the patient may be determined based at least in part on an estimated flow rate of blood exiting the device. Each of left ventricular cardiac output, right ventricular cardiac output, and output of blood from a ventricular assist device may be determined non-invasively.

In those examples where the patient has a left ventricular assist device, if the sum of the left ventricular cardiac output and the output of blood from the left ventricular assist device is less than sum of the right ventricular cardiac output and the output of blood from the right ventricular assist device, then adjusting a parameter may involve increasing an operating speed of the left ventricular assist device. Conversely, if the sum of the left ventricular cardiac output and the output of blood from the left ventricular assist device is greater than sum of the right ventricular cardiac output and the output of blood from the right ventricular assist device, then adjusting a parameter may involve decreasing an operating speed of the left ventricular assist device.

In those examples where the patient has a right ventricular assist device, if the sum of the left ventricular cardiac output and the output of blood from the left ventricular assist device is less than sum of the right ventricular cardiac output and the output of blood from the right ventricular assist device, then adjusting a parameter may involve decreasing an operating speed of the right ventricular assist device. Conversely, if the sum of the left ventricular cardiac output and the output of blood from the left ventricular assist device is greater than sum of the right ventricular cardiac output and the output of blood from the right ventricular assist device, then adjusting a parameter may involve increasing an operating speed of the right ventricular assist device.

In those examples where the patient has a biventricular assist device including each of left and right ventricular assist devices, if the sum of the left ventricular cardiac output and the output of blood from the left ventricular assist device is less than sum of the right ventricular cardiac output and the output of blood from the right ventricular assist device, then adjusting a parameter may involve decreasing an operating speed of the right ventricular assist device and/or increasing an operating speed of the left ventricular assist device. Conversely, if the sum of the left ventricular cardiac output and the output of blood from the left ventricular assist device is greater than sum of the right ventricular cardiac output and the output of blood from the right ventricular assist device, then adjusting a parameter may involve increasing an operating speed of the right ventricular assist device and/or decreasing an operating speed of the left ventricular assist device.

Another aspect of the invention provides for a signal processing circuit for controlling operation of an implanted ventricular assist device. The signal processing circuit may include an input module for receiving one or more signals of a patient from one or more sensors, and a processor for processing the received signals. The processor may be configured to compare a total blood output on a left side of the patient's heart with a total blood output on a right side of the patient's heart, determine the presence or absence of fluid imbalance between the left and right sides of the patient's heart based on the comparison, and if the presence of fluid imbalance is determined, control the implanted ventricular device to restore fluid balance between the left and right sides of the patient's heart.

In some examples, the one or more signals may include a signal measured by a physiological sensor and indicative of atrial pressure, and/or a signal received from a pump of the ventricular assist device and indicative of a flow rate of blood exiting the pump.

In some examples, the signal processing circuit may further include a memory storing a predetermined threshold value, such that the presence of fluid imbalance is determined based on an absolute difference between total blood output on the left and right sides of the patient's heart exceeding the predetermined threshold value.

In those examples where the patient has a left ventricular assist device, the processor may be configured to restore fluid balance by increasing motor speed and/or an amount of power supplied to the left ventricular assist device in response to a determination that total output on the right side of the patient's heart is greater than on the left side, and by decreasing motor speed and/or an amount of power supplied to the left ventricular assist device in response to a determination that total output on the left side of the patient's heart is greater than on the right side.

In those examples where the patient has a right ventricular assist device, the processor may be configured to restore fluid balance by increasing motor speed and/or an amount of power supplied to the right ventricular assist device in response to a determination that total output on the left side of the patient's heart is greater than on the right side, and by decreasing motor speed and/or an amount of power supplied to the right ventricular assist device in response to a determination that total output on the right side of the patient's heart is greater than on the left side.

In those examples where the patient has a biventricular assist device, the processor may be configured to restore fluid balance by increasing motor speed and/or an amount of power supplied to the right ventricular assist device and/or decreasing motor speed and/or an amount of power supplied to the left ventricular assist device in response to a determination that output on the left side of the patient's heart is greater than on the right side, and by decreasing motor speed and/or an amount of power supplied to the right ventricular assist device and/or increasing motor speed and/or an amount of power supplied to the left ventricular assist device in response to a determination that output on the right side of the patient's heart is greater than on the left side.

Yet another aspect of the invention provides for a ventricular assist system having any of the signal processing circuits described herein, one or more a rotary pumps configured to be implantable in fluid communication with the patient's heart to assist blood flow from the heart, and a pump drive circuit in communication with the signal processing circuit and the one or more rotary pumps. The pump drive circuit may be configured to supply power to the pump and control the speed of the pump in response to signals received from the signal processing circuit.

In another aspect of this embodiment, the one or more signals includes a signal measured by a physiological sensor and is indicative of atrial pressure.

In another aspect of this embodiment, the one or more signals includes a signal received from a pump of the ventricular assist device and is indicative of a flow rate of blood exiting the pump.

In another aspect of this embodiment, the device further comprises a memory storing a predetermined threshold value, wherein the presence of fluid imbalance is determined based on a difference between total blood output on the left and right sides of the patient's heart exceeding the predetermined threshold value.

In another aspect of this embodiment, in a patient having both a left ventricular assist device and a right ventricular assist device, the processor is configured to restore fluid balance by: at least one from the group consisting of increasing motor speed and an amount of power supplied to the right ventricular assist device and at least one from the group consisting of decreasing motor speed and an amount of power supplied to the left ventricular assist device in response to a determination that output on the left side of the patient's heart is greater than on the right side, and at least one from the group consisting of decreasing motor speed and an amount of power supplied to the right ventricular assist device and at least one from the group consisting of increasing motor speed and an amount of power supplied to the left ventricular assist device in response to a determination that output on the right side of the patient's heart is greater than on the left side.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
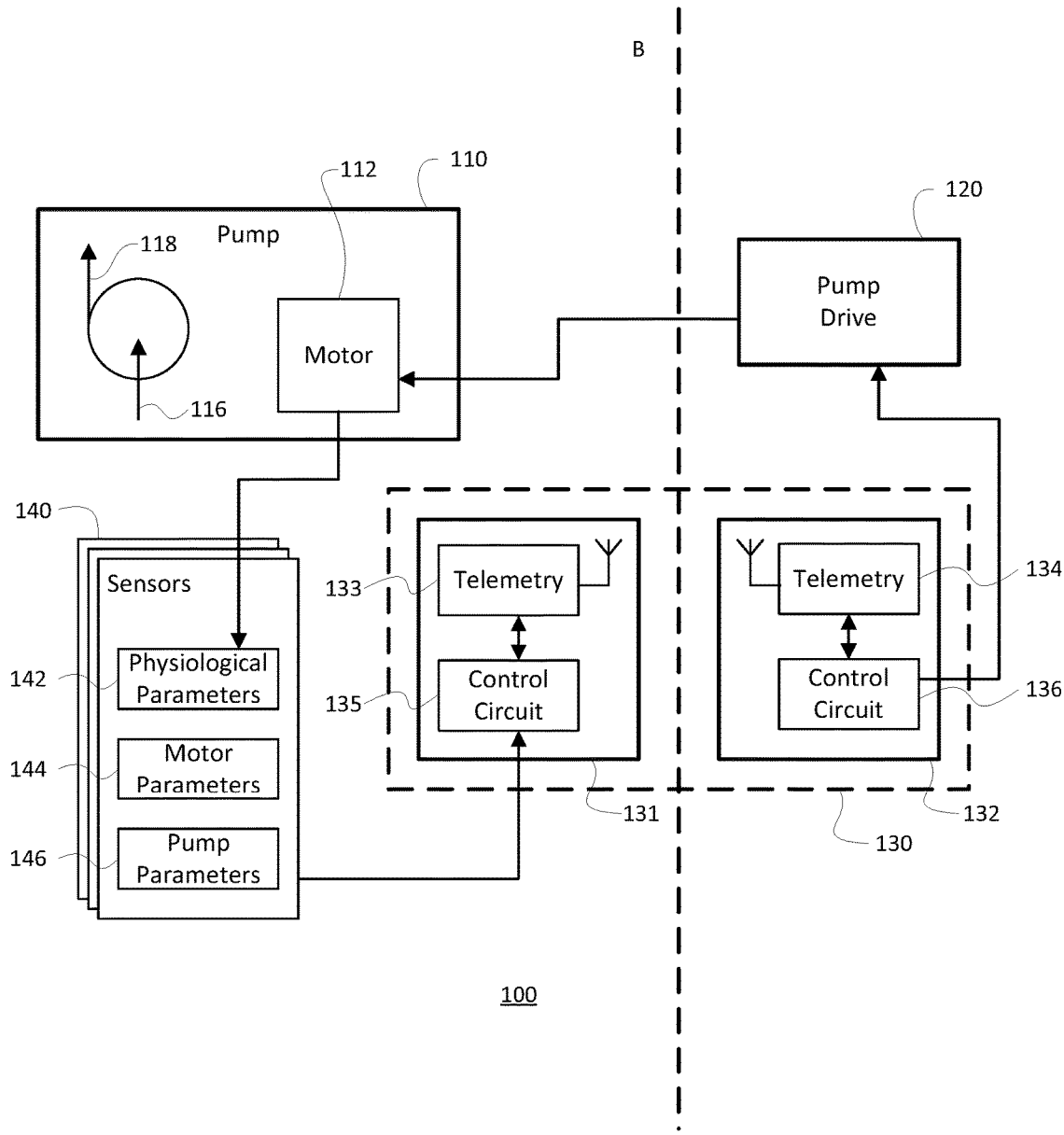
FIG. 1 is a functional block diagram of a VAD in accordance with one embodiment of the invention.

Referring now to the drawings in which like reference designators refer to like elements, as shown in FIG. 1, an implantable blood pump system 100 may include a VAD, such as a rotary pump 110, incorporating a motor 112, that is implantable within the body B of a patient. The term "rotary pump" refers herein to a pump which incorporates a pumping element mounted for rotation in a housing. In one example, the system includes all of the features described in commonly owned U.S. Pat. No. 8,864,644, and co-pending and commonly owned PCT Application No. PCT/US2016/17148 and U.S. Provisional Patent Application Ser. No. 62/245,637, the disclosures of which are incorporated herein in their entirety.

The pump 110 may be a rotary impeller pump having an impeller mounted within a housing, so that the spinning motion of the impeller transfers momentum to the fluid to be pumped. Although the pump 110 and motor 112 are depicted as separate components for clarity of illustration in FIG. 1, in practice these components can be closely integrated with one another. For example, the impeller of the pump 110 may serve as the rotor of the motor 112.

The motor 112 may be a multi-phase brushless direct current, permanent magnet motor arranged to drive the impeller of the pump 110 at a rotational speed prescribed by the motor driver by means of a motor commutation technique such as trapezoidal commutation. These components are arranged so that the pump 110 can be implanted within the body of a mammalian subject such as a human patient, with the inlet 116 in fluid communication with a ventricle of the heart, such as the left ventricle, and with the outlet 118 in fluid communication with an artery, such as the aorta. For example, the pump 110 may be arranged for implantation outside of the heart, and the inlet and outlet may include conduits that can be surgically connected to the ventricle and the aorta. In other arrangements, the pump 110 is arranged so that it may be implanted within the aorta and ventricle. Exemplary implantable pumps are described in detail in U.S. Pat. Nos. 6,264,635, 6,234,772 and 7,699,586; and US Patent Publication No. 20090112312. These patents and published patent applications, which are commonly assigned, are hereby incorporated by reference.

The system 100 may also include a pump drive circuit 120. The pump drive circuit 120 may include ports for one or more output connections and one or more input connections, an electrical storage battery and a motor driver to control the motor. The motor driver may include semiconductor switching elements which are responsive to control signals applied at a control input, so that the current supplied to motor 112 can be controlled. An output connection, such as a cable, may connect the pump drive circuit 120 to the motor 112 of pump 110, so that the motor driver can drive the motor 112 and thus operate the pump 110. In the example of FIG. 1, the pump drive circuit 120 is mounted outside of the patient's body B and is operatively connected to the motor 112 by one or more conductors that penetrate the skin of the patient. In other arrangements, the pump drive circuit may be implanted within the patient's body and may be connected to an external power source using inductive coupling or skin-penetrating conductors, such that the connection between the pump drive circuit and motor does not need to penetrate the patient's skin.

The system 100 may also include a signal processing circuit 130. In the example of FIG. 1, the signal processing circuit 130 is connected to the pump drive circuit 120 to control operation of the pump drive circuit 120, and thereby control operation of the pump 110. The signal processing circuit 130 is also connected to one or more sensors 140 to receive inputs from the sensors, such that operation of the pump may in turn be based on sensor data.

In the example of FIG. 1, the signal processing circuit 130 includes both an internal module 131 implanted inside of the patient's body, and an external module 132 mounted outside of the patient's body B. The modules 131 and 132 may be connected to one another by a suitable signal transmitting arrangement, such as the radio frequency telemetry transmitting/receiving units 133 and 134 shown in FIG. 1, so that signals and data may be interchanged between the modules. Modules 131 and 132 may include conventional data processing elements such as one or more control circuits 135 and 136. The distribution of hardware elements and software functions between these control circuits 135 and 136 can vary. At one extreme, all of the data processing necessary to perform the monitoring and control methods described herein may be performed by the control circuit 136 of the external module 132, with the internal module 131 acting essentially as a conduit for relaying data and signals from the motor 110 to the external module 132 or vice versa. At the other extreme, all of the data processing may be performed by the control circuit 135 of the internal module 131, with the external module acting essentially as a conduit for relaying data and signals from the internal module 131 to the pump drive circuit 120. In such an example, if the pump drive circuit is implanted within the patient's body, the external module 132 may be omitted entirely. Aside from the above extreme examples, given the internal and external modules 131 and 132 capability to relay data and signals between one another, it is well within the ability of those skilled in the art to provide for some data processing to be performed by the control circuitry of one module, while the remaining data processing is performed by the control circuitry of the other module.

The internal module 131 may be connected to receive power from the alternating current supplied by the pump drive circuit 120 to motor 112. The power required to operate the circuitry of the internal module 131 is typically about 3 orders of magnitude less than the power required to drive motor 112. This arrangement is particularly useful where the internal module 131 is physically located in the vicinity of the pump 110, such as being physically coupled to and/or housed in a housing of the pump. In such cases where the internal module 131 of the signal processing circuit 130 is physically located in the vicinity of the pump 110, it may be desirable to provide magnetic shielding between the coils of the pump motor 112 and the circuitry of the internal module 131. In other arrangements, the internal module 131 may be positioned apart from the pump 110. In such arrangements, the signal processing circuitry 130 may receive power from an internal battery (not shown), such as a primary battery or rechargeable battery.

The sensors 140 of the system 100 may include one or more sensors for measuring blood flow and circulation through the patient's cardiovascular system. For example, the one or more sensors may indicate a physiological parameter 142 indicative of blood flow being output by a ventricle of the patient's heart. The sensor may include, for instance, one or more pressure transducers arranged to provide signals indicative of atrial pressure (AP). As atrial pressure rises, so does cardiac output. Therefore, monitoring left atrial pressure (LAP) could be used to determine cardiac output (and thereby total flow) of the left side of the heart, and monitoring right atrial pressure (RAP) could be used to determine cardiac output (and thereby total flow) of the right side of the heart.

Additionally or alternatively, for a given side of the heart provided with a blood pump, one or more sensors may indicate motor parameters 144, such as motor speed or angular position (phase), or back electromotive force ("back EMF" or "BEMF") of the pump, and/or pump parameters 146 such as flow rate of blood exiting the pump and/or pressure differential across the pump. In some instances, a control circuit 135 and/or 136 may be programmed to determine these features non-invasively based on other parameters of the pump (e.g., determining flow rate based on differential pressure, motor current and/or BEMF). Examples of flow rate and pressure determinations based on BEMF are described in detail in US Patent Publication Nos. 2012/0245681, 20140100413, 20140357937. These patents and published patent applications, which are commonly assigned, are hereby incorporated by reference.

Figure 2:
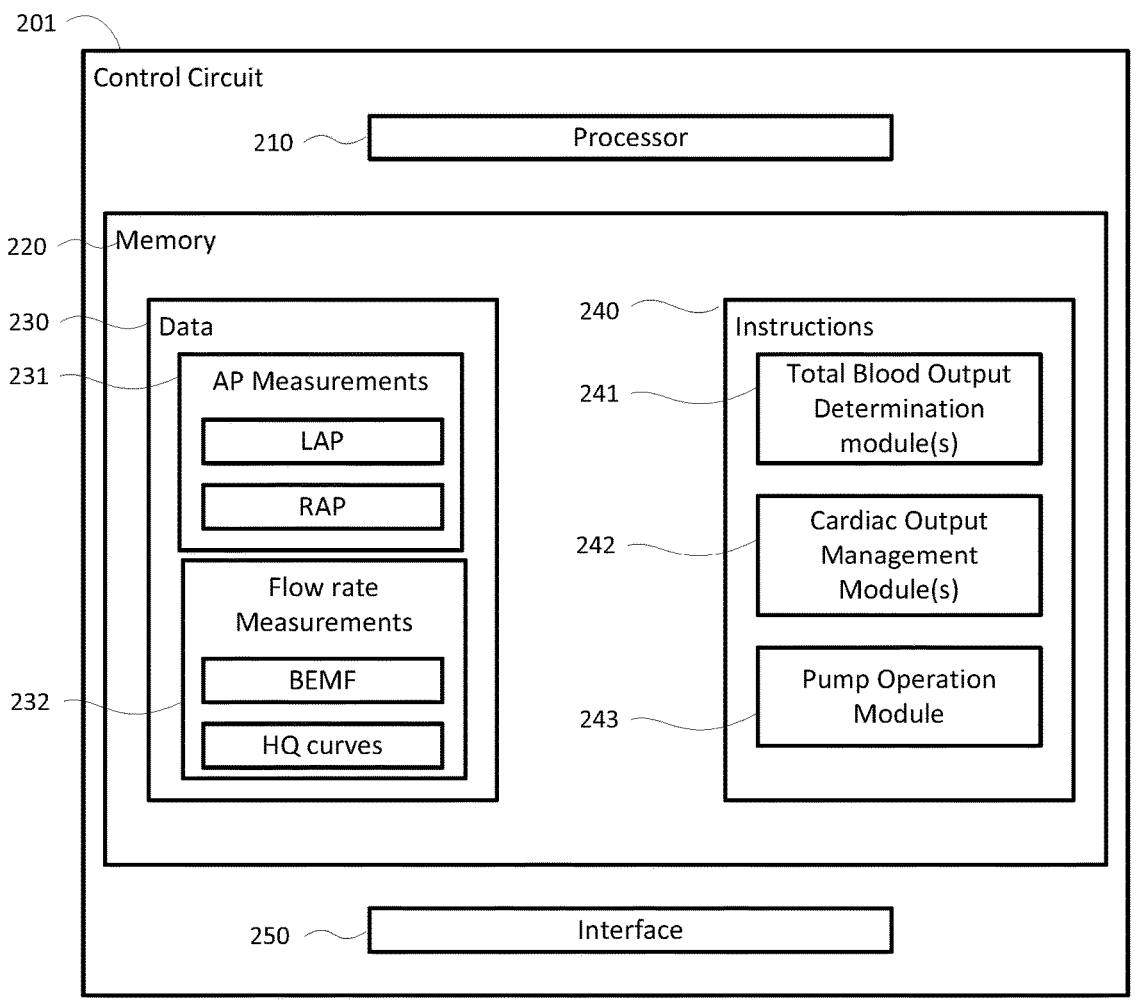
FIG. 2 is a block diagram of a control circuit in accordance with an aspect of the present disclosure.

Referring now to FIG. 2, the functions described in connection with FIG. 2 may be included in the internal control circuit 135, the external control circuit 136, or distributed there between. Additionally, certain functions may be included in both control circuits. The signal processing circuit or control circuit 201 may include a processor 210. The processor 210 may be hardware that performs one or more operations. By way of example only, one or more control units (not shown) coupled to an arithmetic logic unit (ALU) (not shown) and memory 220 may direct the signal processing circuit 201 to carry out program instructions 240 stored in memory 220 at a particular clock rate. The processor 210 may be any standard processor, such as a central processing unit (CPU), or may be a dedicated processor, such as an application-specific integrated circuit (ASIC) or a field programmable gate array (FPGA). While one processor block is shown, the signal processing circuit 201 may also include multiple processors which may or may not operate in parallel.

Memory 220 stores information accessible by processor 210 including instructions 240 for execution by the processor 210 and data 230 which is retrieved, manipulated or stored by the processor 210. The memory 220 may be of any type capable of storing information accessible by the processor, such as a hard-drive, ROM, RAM, CD-ROM, write-capable, read-only, or the like.

Data 230 may be retrieved, stored or modified by processor 210. Although the data of the present disclosure is not limited by any particular data structure, the data 230 may be stored in computer registers, in a relational database as a table having a plurality of different fields and records, such as an XML. The data 230 may also be formatted in any computer readable format such as, but not limited to, binary values, ASCII or EBCDIC (Extended Binary-Coded Decimal Interchange Code). Moreover, any information sufficient to identify the relevant data may be stored, such as descriptive text, proprietary codes, pointers, or information which is used by a function to calculate the relevant data.

The data 230 may include data received from one or a combination of the sensors described herein. By way of example, such data may include AP measurements 231 (e.g., left atrial pressure (LAP), right atrial pressure (RAP)) and/or flow rate measurements 232. In some examples, the flow rate measurements may itself be determined based on other stored data (e.g., BEMF, flow-pressure curves).

The instructions 240 may include any set of instructions to be executed directly (such as machine code) or indirectly (such as scripts) by the processor 210. In that regard, the terms "instructions," "steps" and "programs" may be used interchangeably herein.

The instructions 240 may include one or more modules for analyzing or processing the received data. For example, a total blood output determination module 241 may perform various analyses of AP (indicative of ventricular output), pump flow rate (indicative of pump output) and/or other data, in order to calculate a total blood output on a given side of the patient's heart. In the case of a full assist pump, in which the valve between the patient's ventricle and artery is permanently closed such that all blood flow output by the heart flows through the pump, either one of an AP or pump flow measurement may be used to determine the total blood output. In the case of a partial assist pump, in which the pump operates in parallel with patient's heart, total blood output of the heart may be determined by summing the pump output (e.g., mean flow rate) and the heart output (AP).

The instructions 240 may also include a cardiac output management module 242 for determining pump settings (e.g., pump speed, duty cycle of the pump, etc.) in response to the analyzed cardiac output information of the patient. As discussed in greater detail below, such management may be utilized to maintain or restore fluid balance between the two sides of the heart.

The instructions 240 may also include one or more operation modules 243, each operation module containing a set of instructions for operating the pump (or system) according to a respective mode of operation. Such instructions may dictate an amount of power provided to the motor (e.g., specified duty cycle) and/or a target motor speed.

The signal processing circuit 201 includes one or more interfaces 250 for connecting to inputs (e.g., sensors 140) and outputs (e.g., pump drive circuit 120). The interfaces 250 may include wired and/or wireless connections (e.g., Bluetooth). For components of the signal processing circuit 201 that are adapted to be disposed within the body of the patient, the interface 250 may include known elements for communicating signals through the skin of the patient.

Figure 3:
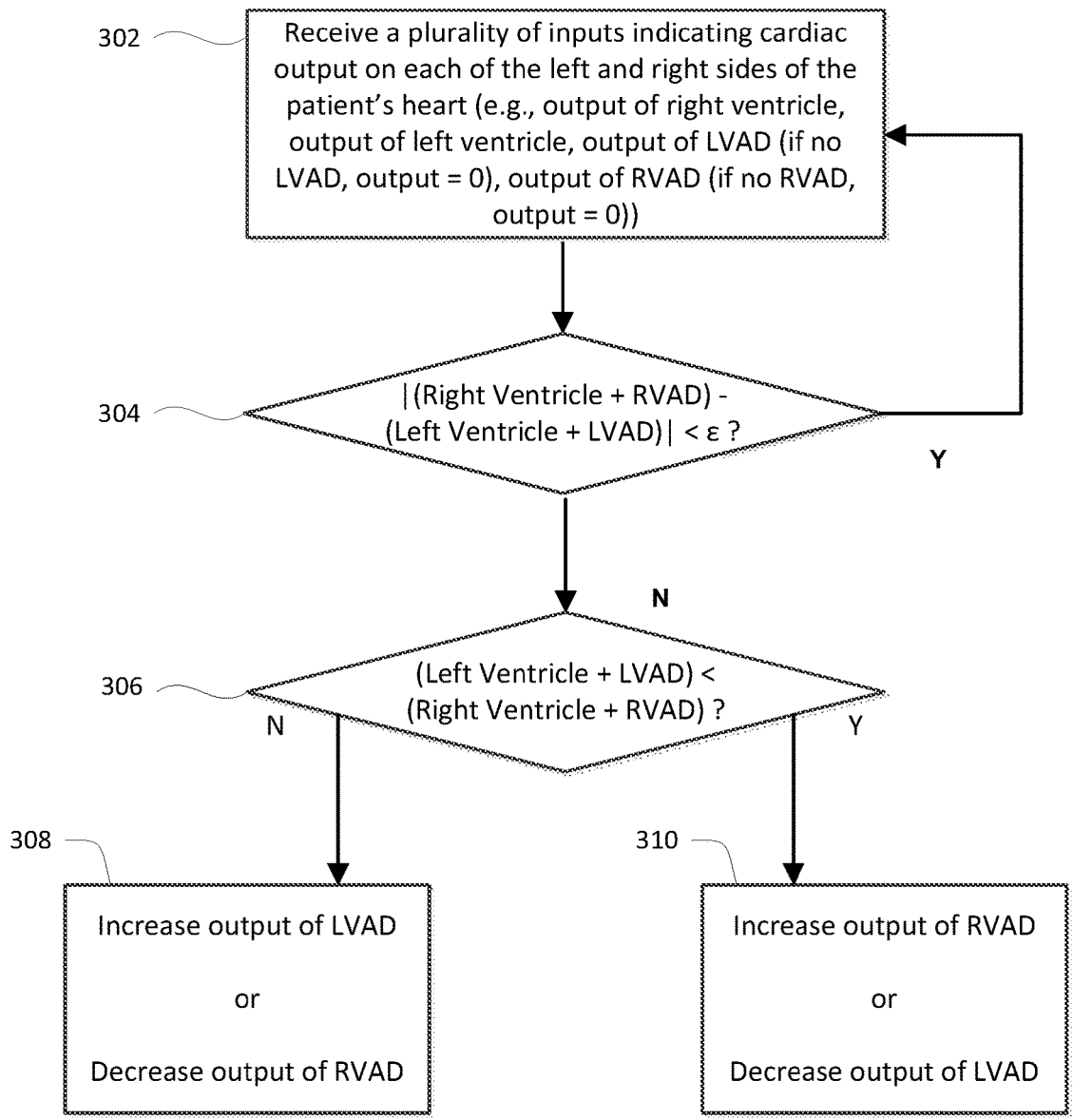
FIG. 3 is flow chart depicting control of one or more VADs based on fluid balance determinations in accordance with an aspect of the present disclosure.

Referring now to FIG. 3, at 302, the signal processing circuit receives a plurality of inputs indicating cardiac output on each of the left and right sides of the patient's heart. As previously described, inputs may be received from either one or a combination of electrode signals (indicating cardiac activity) and pump data (indicating pump activity).

At 304, the signal processing circuit compares the output on the left side of the patient's heart with the output on the right side. Such comparison may be performed using the following equation:

$$|(L_H+L_P)-(R_H+R_P)| \le \varepsilon \qquad (1)$$

in which $L_H$ is blood output from the left ventricle, $R_H$ is blood output from the right ventricle, $L_P$ is blood output from a left ventricular assist device (LVAD), $R_P$ is blood output from a right ventricular assist device (RVAD) and $\varepsilon$ is a predetermined margin of error. The margin of error may be pre-stored in memory of the signal processing circuit. In the above equation, the respective pump outputs may be set to 0 for any side of the heart that is not in communication with a pump. For example, in the case of a patient implanted with an LVAD, $R_P$ may be set to 0. Conversely, in the case of a patient having an implanted RVAD, $L_P$ may be set to 0.

If the comparison at 304 is true, meaning that left and right cardiac output are substantially equal, then the pump continues with the signal processing circuit maintaining the current operation of the pump. The input receiving and comparing of 302 and 304 may be repeatedly performed by the signal processing circuit until an imbalance is detected.

If the comparison at 304 is false, meaning that there is an imbalance between left and right cardiac output, then at 306, the signal processing circuit determined whether output is greater on the left side of the patient's heart or on the right side. Such determination may be made, for example, using the following equation:

$$(L_H+L_P)<(R_H+R_P) \qquad (2)$$

If the comparison at 306 indicates that left output is greater than right output, then at 308, operation of the pump may be adjusted by the signal processing circuit so as to increase right output or decrease left output. In the case of a patient implanted with an LVAD, this may be accomplished by reducing the speed of the pump or reducing an amount of power supplied to the pump. In the case of a patient having an RVAD, this may instead be accomplished by increasing the speed of the pump or increasing an amount of power supplied to the pump.

Conversely, if the comparison at 306 indicates that left output is less than right output, then at 310, operation of the pump may be adjusted by the signal processing circuit so as to increase left output or decrease right output. In the case of a patient implanted with an LVAD, this may be accomplished by increasing the speed of the pump or increasing an amount of power supplied to the pump. In the case of a patient having an RVAD, this may instead be accomplished by reducing the speed of the pump or reducing an amount of power supplied to the pump.

Additionally, in the case of a patient having pumps on both sides of the heart (e.g., a BiVAD), a combination of adjustments to each of the left and right components of the pump may be made in order to yield fluid balance. The left/right adjustments on both sides of the heart may further be tailored to meet a specific output on each side of the heart, instead of just ensuring equal output between the two sides. Optionally, the RAP or the LAP may be set as a baseline atrial pressure which the opposite atrial pressure is balanced with a VAD. For example, a baseline LAP may programmed into the control circuit 201, which the control circuit 201 maintains, in part, by increasing or decreasing pump power to the RVAD. In particular, it may be desirable to maintain the RAP and a desired pressure which may be specific to a particular patient or based on the patient's cardiac pathology. Thus, the control circuit 201 may be configured to increase or decrease power to the RVAD or LVAD to maintain the RAP at the desired pressure. Moreover, the control circuit 201 may be programmed with an upper and lower threshold LAP and/or RAP. For example, if the LAP or RAP exceed a programmed threshold, power may be increased or decreased to the opposite VAD to maintain the RAP or LAP within the programmed upper and lower pressure thresholds.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A signal processing circuit for controlling operation of a single implanted ventricular assist device, comprising:
   an input module for receiving one or more signals of a patient from one or more sensors; and
   a processor for processing the received signals, the processor configured to:
   compare a total blood output on a left side of the patient's heart with a total blood output on a right side of the patient's heart;
   determine at least one from the group consisting of the presence of fluid imbalance between the left and right sides of the patient's heart and the absence of fluid imbalance between the left and right sides of the patient's heart based on the comparison; and
   when the presence of fluid imbalance is determined, control the single implanted ventricular device to restore fluid balance between the left and right sides of the patient's heart.

2. The circuit of claim 1, wherein the one or more signals includes a signal measured by a physiological sensor and is indicative of atrial pressure.

3. The circuit of claim 1, wherein the one or more signals includes a signal received from a pump of the ventricular assist device and is indicative of a flow rate of blood exiting the pump.

4. The circuit of claim 1, further comprising a memory storing a predetermined threshold value, wherein the presence of fluid imbalance is determined based on a difference between total blood output on the left and right sides of the patient's heart exceeding the predetermined threshold value.

5. The circuit of claim 1, wherein, in a patient having a left ventricular assist device as the single implanted device, the processor is configured to restore fluid balance by:
   at least one from the group consisting of increasing motor speed and an amount of power supplied to the left ventricular assist device in response to a determination that total output on the right side of the patient's heart is greater than on the left side, and
   at least one from the group consisting of decreasing motor speed and an amount of power supplied to the left ventricular assist device in response to a determination that total output on the left side of the patient's heart is greater than on the right side.

6. The circuit of claim 1, wherein, in a patient having a right ventricular assist device as the single implanted device, the processor is configured to restore fluid balance by:
   at least one from the group consisting of increasing motor speed and an amount of power supplied to the right ventricular assist device in response to a determination that total output on the left side of the patient's heart is greater than on the right side, and
   at least one from the group consisting of decreasing motor speed and an amount of power supplied to the right ventricular assist device in response to a determination that total output on the right side of the patient's heart is greater than on the left side.

7. A ventricular assist system, comprising:
   a signal processing circuit for controlling operation of a single implanted ventricular assist device, comprising:
   an input module for receiving one or more signals of a patient from one or more sensors; and
   a processor for processing the received signals, the processor being configured to:
   compare a total blood output on a left side of the patient's heart with a total blood output on a right side of the patient's heart;
   determine at least one from the group consisting of the presence of fluid imbalance between the left and right sides of the patient's heart and the absence of fluid imbalance between the left and right sides of the patient's heart based on the comparison; and
   when the presence of fluid imbalance is determined, control the implanted ventricular device to restore fluid balance between the left and right sides of the patient's heart;
   a pump drive circuit in communication with the signal processing circuit and the implanted ventricular device, the pump drive circuit being configured to supply power to the implanted ventricular device and control the speed of the implanted ventricular device in response to signals received from the signal processing circuit.

8. The device of claim 7, wherein the one or more signals includes a signal measured by a physiological sensor and is indicative of atrial pressure.

9. The device of claim 7, wherein the one or more signals includes a signal received from a pump of the ventricular assist device and is indicative of a flow rate of blood exiting the pump.

10. The device of claim 7, further comprising a memory storing a predetermined threshold value, wherein the presence of fluid imbalance is determined based on a difference between total blood output on the left and right sides of the patient's heart exceeding the predetermined threshold value.

* * * * *